United States Patent [19]
Koros et al.

[11] Patent Number: 6,042,542
[45] Date of Patent: Mar. 28, 2000

[54] ROTATABLE RETRACTOR BLADE WITH DETACHABLE CLAMP

[76] Inventors: Tibor B. Koros; Gabriel J. Koros, both of 610 Flinn Ave., Moorpark, Calif. 93021

[21] Appl. No.: 09/190,380

[22] Filed: Nov. 10, 1998

[51] Int. Cl.[7] .................................................. A61B 17/02
[52] U.S. Cl. ........................................... 600/231; 600/232
[58] Field of Search ................................... 600/232, 213, 600/215, 231, 233, 193, 196, 224, 225

[56] References Cited

U.S. PATENT DOCUMENTS

| | | | |
|---|---|---|---|
| 1,401,190 | 12/1921 | Risley ....................................... | 600/232 |
| 1,456,116 | 5/1923 | Bessesen, Sr. ........................... | 600/232 |
| 1,613,141 | 1/1927 | Stein ........................................ | 600/232 |
| 2,642,862 | 6/1953 | Jackson ................................... | 600/232 |
| 2,693,795 | 11/1954 | Grieshaber .............................. | 600/232 |
| 3,509,873 | 5/1970 | Karlin et al. ............................. | 600/231 |
| 3,749,088 | 7/1973 | Kohlmann ................................ | 600/215 |
| 4,010,741 | 3/1977 | Gauthier .................................. | 600/233 |
| 4,421,108 | 12/1983 | Cabrera et al. ........................... | 600/233 |
| 4,865,019 | 9/1989 | Phillips ..................................... | 600/232 |
| 5,365,921 | 11/1994 | Bookwalter .............................. | 600/232 |
| 5,772,583 | 6/1998 | Wright et al. ............................. | 600/232 |
| 5,795,291 | 8/1998 | Koros et al. .............................. | 600/232 |

FOREIGN PATENT DOCUMENTS 824754   2/1958   France ..................................... 600/233

*Primary Examiner*—Paul J. Hirsch
*Attorney, Agent, or Firm*—David O'Reilly

[57] ABSTRACT

A rotatable retractor clamp having a detachable blade clamp. A retractor blade is rotatably secured to a blade clamp by a boss fitting a socket in a clamp body that includes a blade release lever that locks the blade onto the clamp body. After attachment to the clamp, the blade may freely rotate on the blade clamp allowing adjustment after placement of a retractor in an incision. The blade is rotatably held in a socket in the clamp body when installed on a retractor arm but may be easily detached for replacement by a different length blade.

14 Claims, 2 Drawing Sheets

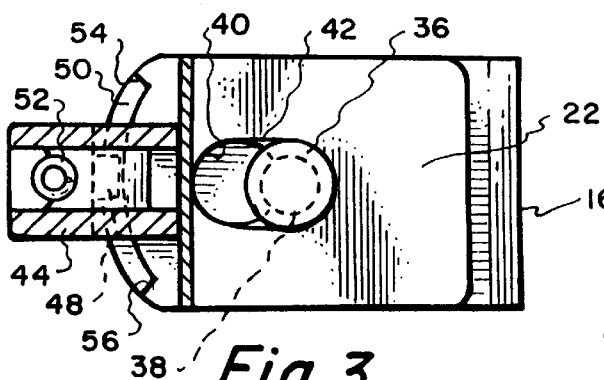
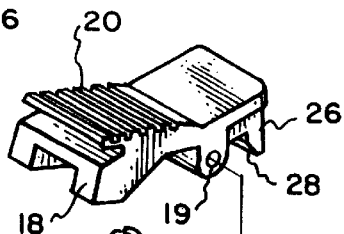
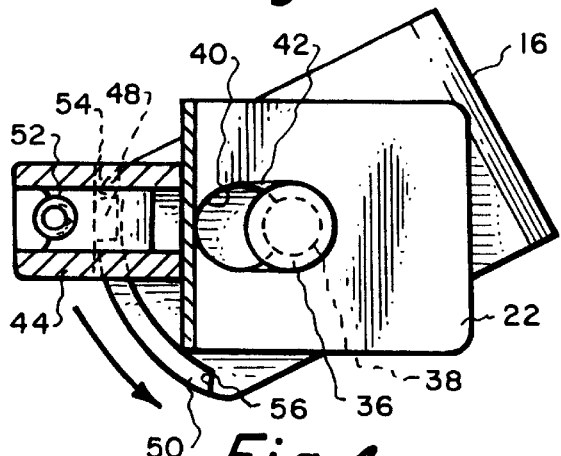
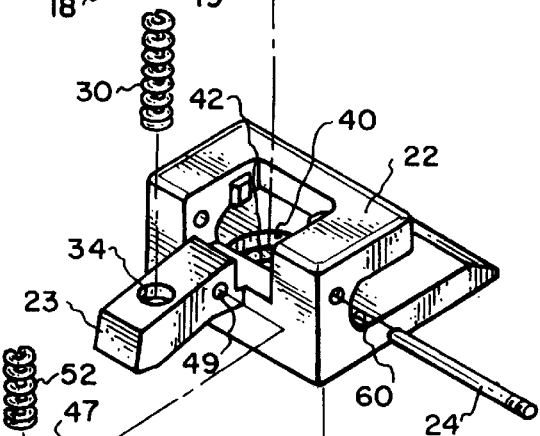
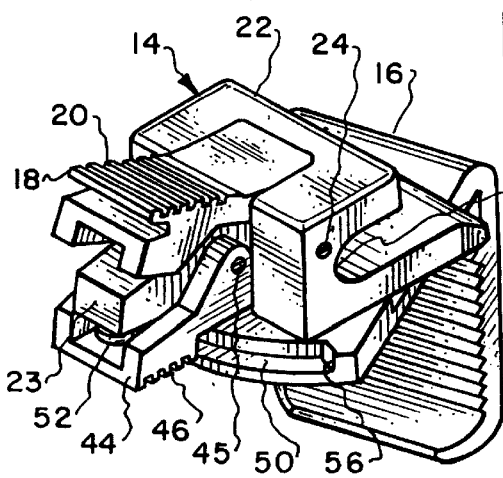
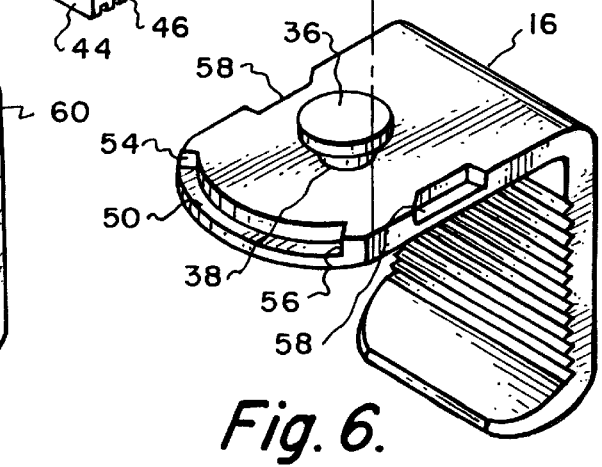
Fig. 3.
Fig. 4.
Fig. 5.
Fig. 6.

ROTATABLE RETRACTOR BLADE WITH DETACHABLE CLAMP

BACKGROUND OF THE INVENTION

1. Field of the Invention

This invention relates to surgical retractor blades and more particularly relates to a surgical retractor rotatable blade with a detachable clamp.

2. Background Information

Retractors are used to hold an incision open when performing surgical procedures. A variety of retractors are used, for example, to perform heart bypass operations and operations such as laminectomies. The retractors come with various length and sizes of blades for retracting tissue from the surgical site.

Surgical retractors are generally comprised of a pair of arms parallel to each other extending from a cross bar. One of the arms is preferably fixed at the end of the cross bar while the other is mounted for movement by crank and gear mechanism along a cross bar to open and close the retractor. Multiple retractor blades are attached to each arm by clamps to retract tissue away from the surgical site. The retractor with or without retractor blades attached are placed in an incision with the arms nearly closed and the movable arm crank open to spread and hold an incision open during surgery. One such surgical retractor is shown and described in U.S. Design Pat. No. 361,381 issued to the same inventors as the device disclosed herein.

Retractor blades are attached to the retractor arms either before or after placement of the retractor and are positioned in the incision to hold tissue away from the surgical site. The retractor blades are generally adjustably mounted on the retractor arms by retractor blade clamps. Preferably the retractor blades are mounted by a clamp gripping a groove or channel in the retractor arms for adjustable movement parallel to the arms. The construction and arrangement of the arm and groove allow multiple blades to be mounted and removed to keep the surgical site clear of surrounding tissue.

Presently retractor blades are clamped onto retractor arms at right angle to the arms. Some retractor blades have an integrally formed clamp for clamping the blade on a retractor arm. The retractor clamp has a mechanism including a tongue for insertion in a channel or groove in the retractable arm from adjustable movement parallel to the arms. Since the retractor arms are at a fixed angle to the retractor cross bar, the position of a retractor blade clamped to a retractor arm is determined by the position of the arm. Therefore, when placed in an incision the surgeon has to jockey the retractor after attaching the blade to get the best retraction of tissue and organs at the surgical site. To adjust the angle of the retractor blades the whole retractor must be moved to achieve the best position. It would be advantageous if the angular position of the retractor blades could be adjusted when securing the blade to the retractor arm.

Also retractor blades that have an integrally formed clamp makes their manufacture and construction complicated and expensive. Another advantageous feature would be the separation of the clamp and the blade so a variety of variable length and design blades could be used with a separate detachable clamp.

It is, therefore, one object of the present invention to provide an improved retractor blade that is adjustable after being mounted on a retractor arm.

Yet another object of the present invention is to provide an improved retractor blade that has an angular adjustment after attachment to a retractor arm.

Still yet another object of the present invention is to provide an improved retractor blade that is detachable from a retractor blade clamp.

Yet another object of the present invention is to provide an improved retractor blade clamp that is constructed to accept a wide variety of retractor blades that can be angularly adjusted after the clamp is attached to a retractor arm.

BRIEF DESCRIPTION OF THE INVENTION

The purpose of the present invention is to provide an improved retractor blade and clamping mechanism that allows angular adjustment of the blade. Also the adjustable blade is preferably detachable from the blade clamp allowing various length and design adjustable blades to be attached to a retractor arm. This patent is related to surgical retractors such as that shown and described and incorporates the blade clamp locking feature of U.S. application Ser. No. 09/045,773 filed Mar. 19, 1998, now U.S. Pat. No. 5,893, 831, by the same inventors as the device disclosed and is incorporated herein by reference.

Retractors for use when performing surgical procedures such as laminectomies, heart bypass surgery or the like are comprised of a frame having a cross bar and a pair of rigid parallel arms extending perpendicular to the cross bar. One of the arms is generally permanently attached to the end of the cross bar while the other arm is adjustable by a precision crank adjustment and gear mechanism. The retractor arms are opened and closed to open and close the incision used during the surgical procedure. Retractor blades are generally attached to the arm by clamps having a locking lever and tongue that fits a longitudinal groove in the retractor arm. Multiple retractor blades are positioned on the retractor arms to hold tissue out of the way during the surgical procedure.

The retractors are used during an operation by placing them over an incision and attaching a blade extended into the body cavity to retract tissue around a surgical site to provide a clear view. Generally the blades are positioned and attached to the retractor arms by clamping them at various locations on the arms. They can be adjustably mounted on the arms for proper positioning in an incision. The retractor blades come in wide variety of lengths and designs and are selected according to the particular operation being performed.

The present invention involves an improvement in the construction and attachment of retractor blades by having the retractor blade removable from the blade clamp. The retractor blade is attached to the retractor clamp by a boss that fits into a key slot in a retractor clamp body allowing the blade to rotate on the clamp. This permits not only interchangeable variety of blades to be attached by a single clamp but also allows the blade to be angularly adjusted after being clamped on the retractor arm.

The retractor clamp is provided with a clamp locking lever and a tongue having a tapered surface or beveled edge as shown and described in U.S. patent application Ser. No. 09/045,773 filed Mar. 19, 1998, now U.S. Pat. No. 5,893, 831, that securely locks the clamp in place on the longitudinal groove in a retractor arm. The body of the retractor clamp is provided with a socket having a key way for receiving a boss formed on a retractor blade. A blade release lever is attached to the body of the blade clamp allowing the retractor blade to be detached from the clamp and exchanged with a different length or different design blade.

A blade is selected for use on a retractor clamp and then attached to the detachable clamp by inserting the boss in the key way and sliding it into the socket in the clamp body. The boss is locked in the socket by a blade release lever on the clamp body. The clamp may then be attached to a retractor arm in a conventional manner with the locking lever tongue engaging an edge in a longitudinal groove on a retractor arm.

If a different blade is needed, the clamp is removed from the retractor arm and the blade release lever operated to detach the blade from the blade clamp. Also, the blade may be rotated through an angle of approximately 60° to adjust the position of the blade. This arrangement provides a unique retractor blade and blade clamp mechanism that is rotatably adjustable as well as detachable from the blade clamp.

The above and other novel features of the invention will be more fully understood from the following detailed description and the accompanying drawings, in which:

BRIEF DESCRIPTION OF THE DRAWINGS

FIG. 3 is a view taken at 3—3 of FIG. 2.

FIG. 4 is a view similar to FIG. 3 illustrating the rotational adjustment of the retractor blade.

FIG. 5 is an isometric view of the rotatable retractor blade and detachable blade clamp shown in an adjusted position.

FIG. 6 is an exploded view illustrating the parts of the rotatable retractor blade and detachable blade clamp mechanism.

DETAILED DESCRIPTION OF THE INVENTION

Figure 1:
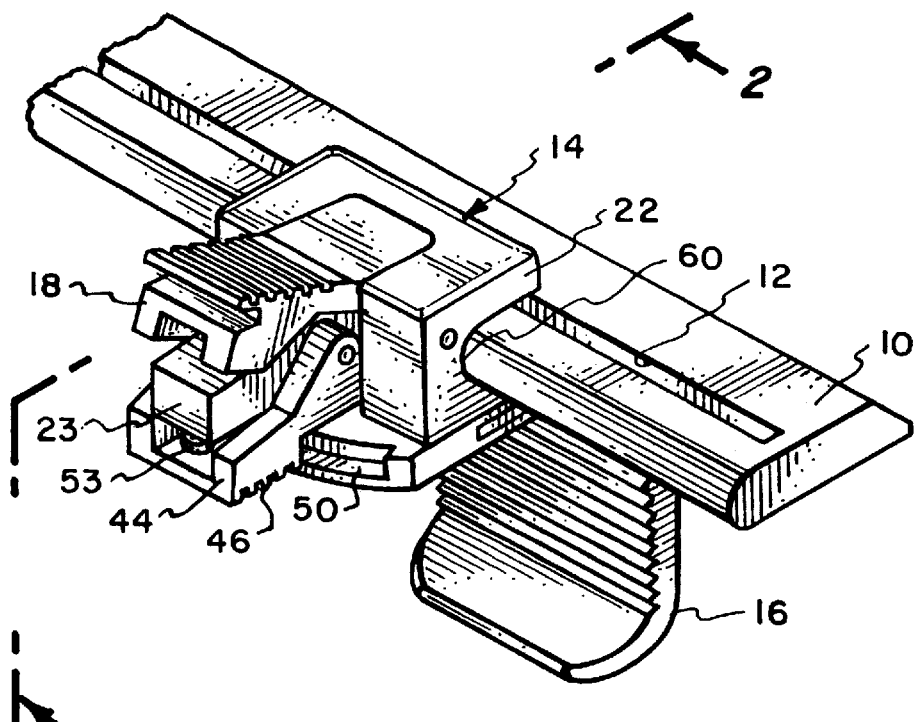
FIG. 1 is an isometric view of a retractor blade showing a detachable blade clamp mounted on a retractor arm.

A portion of a retractor arm 10 having a longitudinal slot 12 for receiving blade clamp 14 having detachable blade 16 is illustrated in FIG. 1. Blade clamp 14 is attached or detached from retractor arm 10 by pressing blade clamp latching lever 18 releasing the clamp as will be described in greater detail hereinafter. Blade clamp 14 with rotatable and detachable blade 16 can be placed anywhere along longitudinal groove 12 in retractor arm 10. Detachable blade 16 is mounted on blade clamp 14 so that it can swivel 30° to 45° left or right from an axis through blade clamp 18 perpendicular to retractor arm 10.

Figure 2:
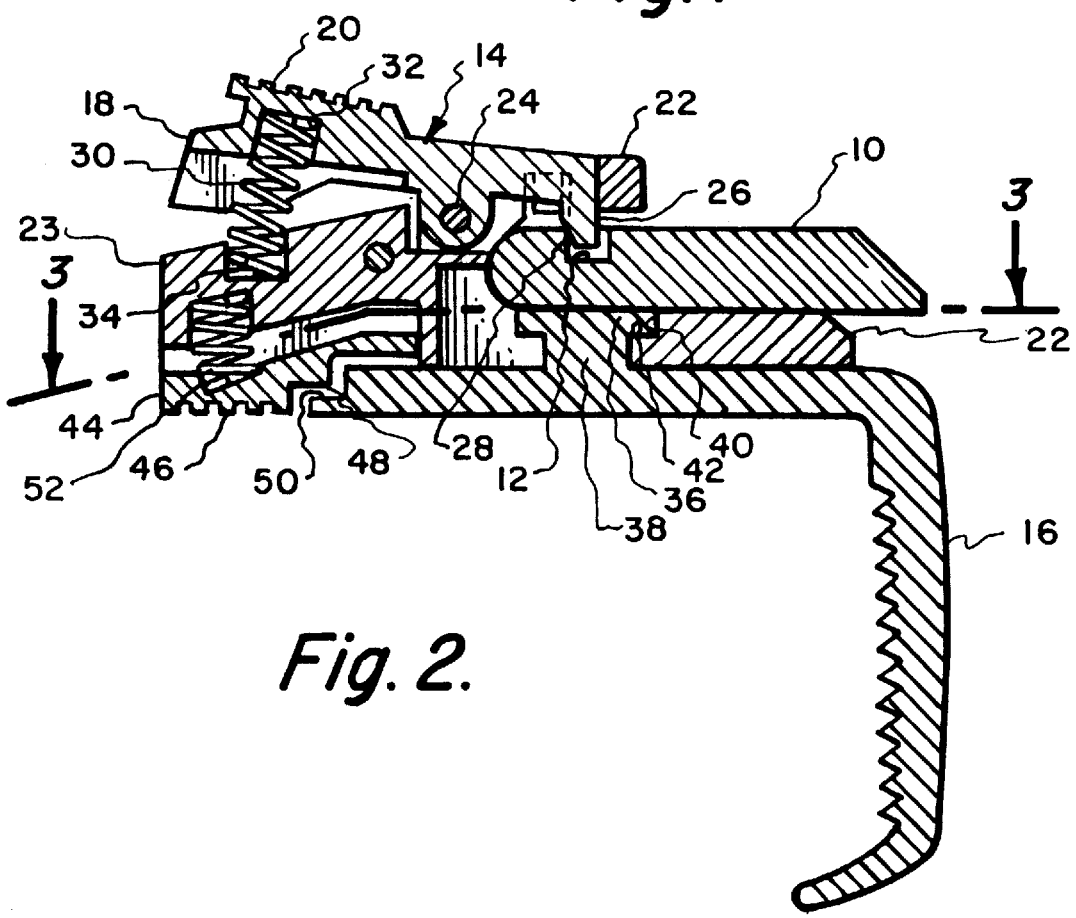
FIG. 2 is a sectional view taken at 2—2 of FIG. 1.

The construction of blade clamp 14 and detachable blade 16 from the sectional view of FIG. 2.

Blade clamp 14 comprised of a blade clamp latching lever 18 having thumb pad 20 is mounted on the clamp body 22 by threaded pin 24. Lever 18 has tongue 26 with a bevel or tapered edge 28 for locking the clamp onto an edge of longitudinal channel 12 in retractor arm 10 as shown and described in prior U.S. application Ser. No. 09/045,773 filed Mar. 19, 1998, now U.S. Pat. No. 5,893,831 by the same inventors as the inventors of the device disclosed herein. Tongue 26 is biased into engagement with the edge of channel 12 by a spring 30 engaging sockets 32 and 34 in lever 18 and clamp body 22, respectively.

Blade 16 is mounted on clamp 14 by a boss 36 mounted on a post 38 constructed to fit a key hole slot 40 having a shoulder 42 (FIG. 3). Post 38 fits into the narrowing portion of key hole slot 40 and is held in place by boss 36 and blade release lever 44 having finger pad 46.

Blade release lever stop 48 engages a rotation guide groove 50 in blade 16 which also limits the rotational movement of the blade as will be described in greater detail hereinafter. Blade release lever stop 48 is biased into blade rotation guide groove 50 by a spring 52 fitting sockets in blade clamp body 22 and blade release lever 46, respectively.

The construction and operation of the rotatable blade 16 detachable from blade clamp 14 can be seen more clearly by reference to FIGS. 3 through 6. Boss 36 on blade 16 is shown engaged in key hole slot 40 on shoulder 42 in FIG. 3. Blade release lever stop 48 slides along rotation guide groove 50 between stops 54 and 56 that limit the rotational movement of blade 16 to approximately 60° or 30° to each side of the axis of post 38 as shown in FIG. 4. Blade release lever stop 48 is shown engaging stop 54 in rotation guide groove 50 also shown in the isometric view of FIG. 5. Blade release lever 44 is secured to mount 23 on clamp body 22 by a threaded pin 45. Blade 16 swivels or rotates between stops 54 and 56 on clamp 14 after installation of retractor arm 10.

The rotatable blade and detachable clamp are assembled as shown in FIG. 6. Clamp locking lever 18 is secured to clamp body 22 by threaded pin 24 engaging holes in clamp body 22 and passing through a bore in flange 19. Spring 30 biases beveled edge 28 of tongue 26 into engagement with longitudinal groove 12 of retractor arm 10.

Blade release lever 44 is attached to blade release lever mount 23 by threaded pin 45 passing through holes in flanges 47 and bore 49 in release lever mount 23. Blade release notches 58 on either sides of blade 16 provide clearance for blade release lever stop 48 allowing boss 36 and post to slide backward for removing the blade from key hole slot 40.

The blade clamp is assembled by mounting clamp release lever 18 on clamp body 22 by inserting threaded pin 24 through the bore in flange 19 on release lever 18 with spring 30 seated in sockets 32 and 34. Blade release lever is then assembled by inserting threaded pin 45 through bores in flanges 47 and bore 49 in release lever mount 23 with spring 52 fitted in sockets between blade release lever 44 and mount 23.

The operation of the rotatable blade 16 and detachable blade clamp 14 is shown in FIGS. 1 and 5. A surgeon can select the length of blade desired and attach it to blade clamp 14 by pressing finger pad 46 on blade release lever 14 after engaging key hole socket 40 in clamp body 22 with boss 36. The blade can now be rotated 90° with blade release lever operated to allow blade release lever stop 48 to engage rotation guide groove when released. Blade clamp 40 with the blade installed may now be secured to retractor arm 10 by sliding the retractor arm into the slot 60 in the blade clamp body 22 with clamp locking lever 18 pressed downward to allow tongue 26 to pass over the surface of retractor arm 10. Release of the clamp locking lever 18 allows tongue 26 to engage longitudinal groove 12 in retractor arm 10 with beveled edge 28 securely engaging an edge of longitudinal groove 12. With the retractor in an incision blade 16 may now be rotated through an angle of approximately 60° to provide the proper tissue retraction without the necessity of moving the retractor frame.

Thus there has been disclosed a unique rotatable retractor blade detachable from a retractor clamp allowing adjustment of a retractor blade after attachment to a retractor. The blade is detachably secured to a blade clamp in a socket allowing rotation through an angle of approximately 60° or more.

Obviously many modifications and variations of the invention are possible in light of the above teachings, therefore, it is understood that the full scope of the invention is not limited to the details disclosed herein but only by the claims appended hereto and may be practiced otherwise than as specifically described.

What is claimed is:

1. An improved retractor blade assembly comprising;

a blade;

blade clamp means for securely clamping said blade on a retractor arm;

rotatable mounting means rotatably mounting said blade on said blade clamp means, said rotatable mounting means comprising;

a boss on said blade;

a socket on said clamp for rotatably receiving said boss on said blade;

blade release lever means for releasing or locking said boss in said socket to rotatably secure said blade on said blade clamp means;

rotatable movement limiting means for limiting the rotatable movement of said blade comprising a guide groove on said blade and a stop on said release lever engaging said guide groove;

whereby the angle of said blade may be adjusted after attachment to a retractor arm with said blade clamp means.

2. The assembly according to claim 1 in which said blade clamp means includes a clamp locking mechanism to prevent movement when said blade clamp means is secured on a retractor arm with a blade attached.

3. The assembly according to claim 2 in which said clamp locking mechanism comprises; a clamp body; a clamp locking lever hingedly attached to said clamp body; a tongue on said clamp locking lever for engaging a longitudinal groove in a retractor arm; and gripping means on said tongue for securely gripping an edge of said longitudinal groove to securely hold said blade clamp means with a blade on said retractor arm.

4. The retractor according to claim 3 in which said gripping means gripping said edge comprises a tapered surface beneath said tongue adapted to engage and grip said edge of said longitudinal groove.

5. The retractor according to claim 1 in which said gripping means gripping said edge comprises a beveled surface on said tongue adapted to engage and grip said edge of said longitudinal groove.

6. The assembly according to claim 7 in which said guide groove limits the angular adjustment to a range of about 60°.

7. The assembly according to claim 6 in which said blade clamp means includes a clamp locking mechanism to prevent movement when said blade clamp means is secured on a retractor arm with a blade attached.

8. The assembly according to claim 7 in which said clamp locking mechanism comprises; a clamp body; a clamp locking lever hingedly attached to said clamp body; a tongue on said clamp locking lever for engaging a longitudinal groove in a retractor arm; and gripping means on said tongue for securely gripping an edge of said longitudinal groove to securely hold said blade clamp means with a blade on said retractor arm.

9. The retractor according to claim 8 in which said gripping means gripping said edge comprises a tapered surface beneath said tongue adapted to engage and grip said edge of said longitudinal groove.

10. The retractor according to claim 9 in which said gripping means gripping said edge comprises a beveled surface on said tongue adapted to engage and grip said edge of said longitudinal groove.

11. An improved retractor blade assembly comprising;

a blade;

blade clamp means for securely clamping said blade on a retractor arm;

rotatable mounting means for rotatably mounting said blade on said blade clamp means, release means for releasably attaching said blade so that interchangeable blades may be easily and quickly attached to and detached from said blade clamp means, lock means for locking said blade in an adjusted rotated position;

said rotatable mounting means including rotation limiting means for limiting the maximum rotation of said blade;

whereby interchangeable blades may be easily and quickly attached and detached from said blade clamp means and rotationally adjusted.

12. The improved retractor blade assembly according to claim 11 in which said rotatable mounting means comprises; a boss on said blade; and a socket on said blade clamp means for rotatably receiving said boss.

13. The improved retractor blade assembly according to claim 12 in which said release means locks said boss in said socket.

14. The improved retractor blade assembly according to claim 13 in which said release means comprises a release lever on said blade clamp means; said release lever having a stop engaging a guide groove on said blade to lock said boss in said socket and limit rotational movement of said blade.

* * * * *